United States Patent
Kim et al.

(10) Patent No.: US 11,400,056 B2
(45) Date of Patent: Aug. 2, 2022

(54) PHARMACEUTICAL COMPOSITION COMPRISING GALLSTONE SOLUBILIZER FOR TREATMENT OF GALLBLADDER DISEASE

(71) Applicant: SurgiNex Co., Ltd., Seoul (KR)

(72) Inventors: Say June Kim, Daejeon (KR); Kwan Young Jeong, Daejeon (KR); Ok Hee Kim, Gyeryong-si (KR); Seok Jun Jo, Iksan-si (KR); Min Jin Yoo, Gimhae-si (KR)

(73) Assignee: SurgiNex Co., Ltd., Seoul (KR)

( * ) Notice: Subject to any disclaimer, the term of this patent is extended or adjusted under 35 U.S.C. 154(b) by 443 days.

(21) Appl. No.: 16/461,785

(22) PCT Filed: Sep. 19, 2017

(86) PCT No.: PCT/KR2017/010249
§ 371 (c)(1),
(2) Date: Sep. 23, 2019

(87) PCT Pub. No.: WO2018/056669
PCT Pub. Date: Mar. 29, 2018

(65) Prior Publication Data
US 2020/0030257 A1 Jan. 30, 2020

(30) Foreign Application Priority Data
Sep. 20, 2016 (KR) ........................ 10-2016-0120240

(51) Int. Cl.
*A61P 1/16* (2006.01)
*A61K 31/08* (2006.01)
*A61K 31/12* (2006.01)
*A23L 33/10* (2016.01)

(52) U.S. Cl.
CPC .............. *A61K 31/12* (2013.01); *A23L 33/10* (2016.08); *A61P 1/16* (2018.01); *A61K 31/08* (2013.01)

(58) Field of Classification Search
CPC ................................. A61K 31/08; A61P 1/16
See application file for complete search history.

(56) References Cited

U.S. PATENT DOCUMENTS

| 7,157,578 B2 | 1/2007 | Gilligan |
| 2004/0014760 A1 | 1/2004 | Gilligan |
| 2014/0039007 A1 | 2/2014 | Tully et al. |

FOREIGN PATENT DOCUMENTS

| CN | 102936282 A | 2/2013 |
| EP | 1894928 A1 | 3/2008 |
| KR | 1997-0058710 A | 8/1997 |
| KR | 10-2016-0030983 A | 3/2016 |

OTHER PUBLICATIONS

Mundal et al., Synthetic studies toward the citrinadin A and B core architecture. Organic Letts. vol. 15(19), pp. 4952-4955 (Year: 2013).*
International Search Report of corresponding PCT Patent Application No. PCT/KR2017/010249, which is parent—3 pages (dated Feb. 2, 2018).

* cited by examiner

*Primary Examiner* — Barbara P Badio
(74) *Attorney, Agent, or Firm* — Knobbe, Martens, Olson & Bear, LLP

(57) ABSTRACT

The present disclosure relates to a pharmaceutical composition for treating gallbladder disease containing a gallstone-dissolving agent, and more specifically, to a pharmaceutical composition for treating gallbladder disease containing a gallstone-dissolving agent which dissolves gallstone, a cause of the gallbladder disease, and thus has an excellent effect of alleviating or treating any one or more symptoms selected from the group consisting of asymptomatic cholelithiasis, biliary colic, cholecystitis, choledocholithiasis, and biliary pancreatitis.

6 Claims, 3 Drawing Sheets

PHARMACEUTICAL COMPOSITION COMPRISING GALLSTONE SOLUBILIZER FOR TREATMENT OF GALLBLADDER DISEASE

TECHNICAL FIELD

The present disclosure relates to a pharmaceutical composition for treating gallbladder disease containing a gallstone-dissolving agent, and more particularly to a pharmaceutical composition for treating gallbladder disease containing a gallstone-dissolving agent having the effect of dissolving gallstone, a cause of the gallbladder disease.

BACKGROUND ART

The gallbladder is located under the liver and on the right side of the stomach and connects the liver to the duodenum. The role of the gallbladder is to store bile secreted from the liver. After food is mixed in the stomach, it goes down to the small intestine after passing through the duodenum. Digestive enzymes from the gallbladder and digestive enzymes from the pancreas meet together in the duodenum and go down to the small intestine together with food through a duct connected to the duodenum, and the food is absorbed in the small intestine in earnest by the action of the digestive enzymes.

Meanwhile, cholelithiasis which is the most common type of gallbladder disease occurs when the liquid stored in the gallbladder hardens into pieces of stone-like material. Cholelithiasis is a disease in which stones are formed in the gallbladder or bile duct. Cholelithiasis affects about 10% of the total population in the West and about 4% of the population in Korea.

Here, gallstones are divided into cholesterol stones and pigmented stones based on the chemical composition thereof, and pigmented stones are divided into black-pigment and brown-pigment stones.

Cholesterol stones are usually yellow-green in appearance, and made primarily of hardened cholesterol, and account for 80% of gallstones. Meanwhile, pigment stones are small, dark stones made of bilirubin (a type of waste produced by degradation of hemoglobin contained in erythrocytes). Gallstones can be as small as a grain of sand or as large as a golf ball. The gallbladder can develop just one large stone, hundreds of tiny stones, or a combination of the two.

When gallstones come out of the gallbladder and get stuck in any part of the duct that carries bile from the liver to the small intestine, they can block the normal flow of bile.

To treat this cholelithiasis, surgical or non-surgical therapy is used. In particular, as the non-surgical therapy, oral gallstone dissolution therapy or direct gallstone dissolution therapy is known.

Regarding the oral gallstone dissolution therapy, drugs that are used to dissolve gallstones using drugs made of bile acid include ursodiol (e.g., URSA) and chenodiol, which are particularly effective against small cholesterol stones. When these drugs are used, it may take several months or years until all gallstones are dissolved. The two drugs have some side effects, including diarrhea with weak symptoms, abdominal pain, and abdominal discomfort, and chenodiol has the problem of temporarily increasing blood cholesterol levels and liver enzyme levels.

Meanwhile, the gallstone dissolution therapy refers to injecting a drug directly into the gallbladder to dissolve cholesterol stone. This method can dissolve several gallstones within a few days, but it has been reported that this method may cause irritation and complications.

Accordingly, as a conventional art related to a gallstone-dissolving agent, Japan Patent No. 4593918 relates to a kind of drug composition, which has the effect of promoting bile secretion and dissolving gallstone, and a method for preparing the same, and it discloses a drug composition, which mainly contains mint oil and geranium oil at a volume ratio of 2 to 6:1 to 2 and relieves smooth muscle spasms. Japanese Patent Application Laid-Open Publication No. 1997-059162 relates to a pharmaceutical composition for treating calcium gallstone containing, as active ingredients, ursodeoxycholic acid, amino acid, citric acid, and their sodium salts, and it provides a pharmaceutical composition for dissolving calcium gallstones, in which the composition has resistance to human pancreatic enzymes or coryglycine hydrase and has excellent oral absorbability.

DISCLOSURE

Technical Problem

It is an object of the present disclosure to provide a pharmaceutical composition for preventing or treating gallbladder disease, which has an excellent ability to dissolve gallstones and is less toxic.

Technical Solution

Hereinafter, various embodiments described herein will be described with reference to figures. In the following description, numerous specific details are set forth, such as specific configurations, compositions, and processes, etc., in order to provide a thorough understanding of the present disclosure. However, certain embodiments may be practiced without one or more of these specific details, or in combination with other known methods and configurations. In other instances, known processes and preparation techniques have not been described in particular detail in order to not unnecessarily obscure the present disclosure. Reference throughout this specification to "one embodiment" or "an embodiment" means that a particular feature, configuration, composition, or characteristic described in connection with the embodiment is included in at least one embodiment of the present disclosure. Thus, the appearances of the phrase "in one embodiment" or "an embodiment" in various places throughout this specification are not necessarily referring to the same embodiment of the present disclosure. Additionally, the particular features, configurations, compositions, or characteristics may be combined in any suitable manner in one or more embodiments.

Unless otherwise stated in the specification, all the scientific and technical terms used in the specification have the same meanings as commonly understood by those skilled in the technical field to which the present disclosure pertains.

According to one embodiment of the present disclosure, there is provided a pharmaceutical composition for preventing or treating gallbladder disease containing, as an active ingredient, a compound represented by the following formula 1 or formula 2:

[Formula 1]

-continued

[Formula 2]

wherein $R_1$ is a $C_1$-$C_6$ alkyl group;

$R_2$ is selected from the group consisting of a $C_5$-$C_{10}$ aryl group, a $C_5$-$C_{10}$ heteroaryl group, and —C(=O)$R_5$;

$R_3$ is a $C_1$-$C_6$ alkyl group;

$R_4$ is selected from the group consisting of a $C_1$-$C_6$ alkyl group and a $C_3$-$C_6$ cycloalkyl group;

$R_5$ is a $C_5$-$C_8$ aryl group or a $C_5$-$C_8$ heteroaryl group; and the alkyl group of $R_1$ and $R_3$, aryl group and heteroaryl group of $R_2$, the alkyl group and cycloalkyl group of $R_4$, and the aryl group and heteroaryl group of $R_5$ may be each independently unsubstituted or substituted with one or more $C_1$-$C_6$ alkyl groups and if substituted with a plurality of substituents, these substituents may be identical or different.

In the present disclosure, $R_1$ is preferably a methyl group, but is not limited thereto.

In the present disclosure, $R_2$ is preferably selected from the group consisting of a pyridinyl group, a pyrimidinyl group and a benzoyl group, but is not limited thereto.

In the present disclosure, $R_3$ is preferably a methyl group, but is not limited thereto.

In the present disclosure, $R_4$ is preferably a cyclopropyl group, but is not limited thereto.

In the present disclosure, the compound represented by formula 1 is preferably 2-methoxy-6-methylpyridine, or methyl 3-methylbenzoate, but is not limited thereto.

In the present disclosure, the compound represented by formula 2 is preferably 1-cyclopropylethanone, but is not limited thereto.

In the present disclosure, the compound represented by formula 1 or formula 2 may have a boiling point of 80 to 160° C.

In the present disclosure, the gallstone may include cholesterol stone or pigmented stone.

In the present disclosure, the gallbladder disease may include one or more diseases selected from the group consisting of asymptomatic cholelithiasis, biliary colic, cholecystitis, choledocholithiasis, and biliary pancreatitis, but is not limited thereto.

According to another embodiment of the present disclosure, there is provided a food composition for alleviating gallbladder disease containing a compound represented by the following formula 1 or formula 2:

[Formula 1]

[Formula 2]

wherein $R_1$ is a $C_1$-$C_6$ alkyl group;

$R_2$ is selected from the group consisting of a $C_1$-$C_6$ alkyl group, a $C_5$-$C_{10}$ aryl group, a $C_5$-$C_{10}$ heteroaryl group, and —C(=O)$R_5$;

$R_3$ is a $C_1$-$C_6$ alkyl group;

$R_4$ is selected from the group consisting of a $C_1$-$C_6$ alkyl group and a $C_3$-$C_6$ cycloalkyl group;

$R_5$ is a $C_5$-$C_8$ aryl group or a $C_5$-$C_8$ heteroaryl group; and the alkyl group of $R_1$ and $R_3$, the alkyl group, aryl group and heteroaryl group of $R_2$, the alkyl group and cycloalkyl group of $R_4$, and the aryl group and heteroaryl group of $R_5$ may be each independently unsubstituted or substituted with one or more $C_1$-$C_6$ alkyl groups and if substituted with a plurality of substituents, these substituents may be identical or different.

Unless otherwise specified, the term '$C_1$-$C_6$ alkyl' as used herein means a straight-chain or branched hydrocarbon radical having 1 to 6 carbon atoms. Examples thereof include, but are not limited to, methyl, ethyl, propyl, iso-propyl, n-butyl, sec-butyl, t-butyl, n-pentyl, n-hexyl, etc.

Unless otherwise specified, the term 'aryl' as used herein refers to a $C_5$ to $C_{10}$ mono- or poly-cyclic carbocyclic ring system having one or more aromatic rings, fused or non-fused, and examples of aryl include, but are not limited to, phenyl, naphthyl, tetrahydronaphthyl, indenyl, anthracenyl, etc.

Unless otherwise specified, the term 'heteroaryl' as used herein refers to a $C_5$ to $C_{10}$ monocyclic, bicyclic or higher aromatic group containing at least one (e.g., 1 to 4) heteroatoms selected from among O, N and S. Examples of the monocyclic heteroaryl include, but are not limited to, thiazolyl, oxazolyl, thiophenyl, furanyl, pyrroyl, imidazolyl, isoxazolyl, pyrazolyl, triazolyl, thiadiazolyl, tetrazolyl, oxadiazolyl, pyridinyl, pyridazinyl, pyrimidinyl, pyrazinyl, and groups similar thereto. Examples of bicyclic heteroaryl include, but are not limited to, indolyl, benzothiophenyl, benzofuranyl, benzimidazolyl, benzoxazolyl, benzoisoxazolyl, benzothiazolyl, benzothiadiazolyl, benzotriazolyl, quinolinyl, isoquinolinyl, furinyl, furopyridinyl, and groups similar thereto.

Advantageous Effects

The compound provided in the present disclosure has an excellent ability to dissolve gallstone, a cause of gallbladder disease, and has no toxicity for gallbladder epithelial cells. Thus, it may be useful as an agent for preventing or treating various diseases associated with gallbladder disease.

Best Mode

According to one embodiment of the present disclosure, there is provided a pharmaceutical composition for preventing or treating gallbladder disease containing, as an active ingredient, a compound represented by the following formula 1 or formula 2:

[Formula 1]

[Formula 2]

wherein
$R_1$ is a $C_1$-$C_6$ alkyl group;
$R_2$ is selected from the group consisting of a $C_1$-$C_6$ alkyl group, $C_5$-$C_{10}$ aryl group, a $C_5$-$C_{10}$ heteroaryl group, and —C(=O)$R_5$;
$R_3$ is a $C_1$-$C_6$ alkyl group;
$R_4$ is selected from the group consisting of a $C_1$-$C_6$ alkyl group and a $C_3$-$C_6$ cycloalkyl group;
$R_5$ is a $C_5$-$C_8$ aryl group or a $C_5$-$C_8$ heteroaryl group; and
the alkyl group of $R_1$ and $R_3$, the alkyl group, aryl group and heteroaryl group of $R_2$, the alkyl group and cycloalkyl group of $R_4$, and the aryl group and heteroaryl group of $R_5$ may be each independently unsubstituted or substituted with one or more $C_1$-$C_6$ alkyl groups and if substituted with a plurality of substituents, these substituents may be identical or different.

Mode for Disclosure

Hereinafter, preferred embodiments of the present disclosure will be described. However, the embodiments of the present disclosure may be modified into various other forms, and the scope of the present disclosure is not limited to the embodiments described below. In addition, the embodiments of the present disclosure are provided to fully convey the scope of the present disclosure to those skilled in the art.

According to one embodiment of the present disclosure, there is provided a pharmaceutical composition for preventing or treating gallbladder disease containing, as an active ingredient, a compound represented by the following formula 1 or formula 2:

[Formula 1]

[Formula 2]

wherein
$R_1$ is a $C_1$-$C_6$ alkyl group;
$R_2$ is selected from the group consisting of a $C_5$-$C_{10}$ aryl group, a $C_5$-$C_{10}$ heteroaryl group, and —C(=O)$R_5$;
$R_3$ is a $C_1$-$C_6$ alkyl group;
$R_4$ is selected from the group consisting of a $C_1$-$C_6$ alkyl group and a $C_3$-$C_6$ cycloalkyl group;
$R_5$ is a $C_5$-$C_8$ aryl group or a $C_5$-$C_8$ heteroaryl group; and
the alkyl group of $R_1$ and $R_3$, the aryl group and heteroaryl group of $R_2$, the alkyl group and cycloalkyl group of $R_4$, and the aryl group and heteroaryl group of $R_5$ may be each independently unsubstituted or substituted with one or more $C_1$-$C_6$ alkyl groups and if substituted with a plurality of substituents, these substituents may be identical or different.

In the present disclosure, when $R_1$ is a methyl group, the compound is less toxic and shows a high gallstone dissolution rate. Thus, $R_1$ is preferably a methyl group, but is not limited thereto.

In the present disclosure, when $R_2$ is selected from the group consisting of a pyridinyl group, a pyrimidinyl group and a benzoyl group, the compound is less toxic and shows a high gallstone dissolution rate. Thus, $R_2$ is preferably selected from the group consisting of a pyridinyl group, a pyrimidinyl group and a benzoyl group, but is not limited thereto.

In the present disclosure, when $R_3$ is a methyl group, the compound is less toxic and shows a high gallstone dissolution rate. Thus, $R_3$ is preferably a methyl group, but is not limited thereto.

In the present disclosure, when $R_4$ is a cyclopropyl group, the compound is less toxic and shows a high gallstone dissolution rate. Thus, $R_4$ is preferably a cyclopropyl group, but is not limited thereto.

In the present disclosure, the compound represented by formula 1 is preferably 2-methoxy-6-methylpyridine, or methyl 3-methylbenzoate, but is not limited thereto.

In the present disclosure, the compound represented by formula 2 is preferably 1-cyclopropylethanone, but is not limited thereto.

In the present disclosure, the compound can dissolved gallstones, thereby preventing or treating various gallbladder diseases that can be caused by gallstones.

Here, the gallstone may include cholesterol stone or pigment stone.

In the present disclosure, the 2-methoxy-6-methylpyridine, methyl 3-methylbenzoate and 1-cyclopropylethanone compounds can effectively dissolve cholesterol stones and pigmented stones.

In addition, in the present disclosure, the compound represented by formula 1 or formula 2 is preferable because it does not form an epoxide even when it is stored for a long period of time. In addition, it has a boiling point of 80 to 160° C., and thus has an advantage in that it is not volatilized in the body or the rate of vaporization thereof is extremely low, indicating that it has less side effects.

In the present disclosure, the gallbladder disease to be prevented or treated with the compound represented by formula 1 or formula 2 may include one or more disease selected from the group consisting of asymptomatic cholelithiasis, biliary colic, cholecystitis, choledocholithiasis, and biliary pancreatitis, but is not limited thereto.

As used herein, the term 'asymptomatic cholelithiasis' means a condition in which the patient is unaware of the presence of gallstones because the gallstones are asymptomatic.

As used herein, the term 'biliary colic' refers to a severe abdominal pain that starts from below the right rib and spreads to the abdomen and waist with nausea and vomiting and makes the patient feel severe pain for 30 minutes to several hours. Often, biliary colic appears after eating greasy food and makes the patient feel chronic nausea.

As used herein, the term 'cholecystitis' refers to is a serious disease which is caused by infection or inflammation in the gallbladder and which occurs while the bile duct is clogged. It has symptoms which are similar to but longer lasting than those of biliary colic. Cholecystitis involves fever, makes the patient feel cold, and shows increased leukocyte count upon examination.

As used herein, the term 'choledocholithiasis' refers to a disease caused by gallstones from the gallbladder. Gallstones from the gallbladder can also pass through the bile ducts without causing any special problems, but when get stuck in the bile ducts, cause problems, causing severe abdominal pain and jaundice and sometimes causing a life-threatening infection.

As used herein, the term 'biliary pancreatitis' refers to a disorder which occurs when gallstones cause inflammation while passing through the pancreatic duct after passage through the bile ducts. Biliary pancreatitis is accompanied by nausea and vomiting and causes sporadic abdominal pain.

As used herein, the term 'preventing' refers to all actions that suppress gallbladder disease or delay the onset thereof by administering the pharmaceutical composition of the present disclosure.

As used herein, the term 'treating' refers to all actions that alleviate or beneficially change gallbladder disease symptoms by administering the pharmaceutical composition of the present disclosure.

In the present disclosure, the pharmaceutical composition may be in the form of capsules, tablets, granules, injectable solutions, ointments, powders or beverages, and the pharmaceutical composition may be for administration to humans.

For use, the pharmaceutical compositions of the present disclosure may be formulated as oral dosage forms, such as powders, granules, capsules, tablets or aqueous suspensions, external dosage forms, suppositories, and sterile injectable solutions according to conventional methods, but is not limited thereto. The pharmaceutical composition of the present disclosure may contain pharmaceutically acceptable carriers. Pharmaceutically acceptable carriers that may be used for oral administration include binders, lubricants, disintegrants, excipients, solubilizers, dispersing agents, stabilizers, suspending agents, pigments, fragrances, etc. For injection, buffers, preservatives, analgesic agents, solubilizers, isotonic agents, stabilizers, etc., may be used, and for topical administration, bases, excipients, lubricants, preservatives, etc. may be used. The pharmaceutical composition of the present disclosure may be prepared as various formulations by mixing with the pharmaceutically acceptable carriers as described above. For example, for oral administration, the pharmaceutical composition may be formulated in the form of tablets, troches, capsules, elixirs, suspensions, syrups, wafers, etc., and for injection, it may be formulated as unit dosage ampoules or multi-dose vials. In addition, the pharmaceutical composition of the present disclosure may be formulated as solutions, suspensions, tablets, capsules, sustained-release preparations, or the like.

Meanwhile, examples of carriers, excipients and diluents suitable for formulation include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, mineral oil and the like. In addition, the pharmaceutical composition may further contain a filler, an anticoagulant, a lubricant, a wetting agent, a fragrance, an emulsifier, a preservative, etc.

The routes of administration of the pharmaceutical composition according to the present disclosure include, but are not limited to, oral, intravenous, intramuscular, intra-arterial, intra-marrow, intrathecal, intracardiac, transdermal, subcutaneous, intraperitoneal, intranasal, intestinal, local, sublingual or intrarectal routes. Oral or parenteral administration is preferred.

In the present disclosure, "parenteral" includes subcutaneous, transdermal, intravenous, intramuscular, intra-articular, intra-synovial, intrasternal, intradural, intra-lesional and intra-cranial injection or infusion techniques. The pharmaceutical composition of the present disclosure may also be formulated as suppositories for intrarectal administration.

The pharmaceutical composition of the present disclosure may vary depending on various factors, including the activity of a specific compound used, the patient's age, body weight, general health, sex, diet, the period of administration, the route of administration, excretion rate, the drug content, and the severity of a specific disease to be prevented or treated. The dose of the pharmaceutical composition may be suitably selected by a person skilled in the art depending on the patient's condition, body weight, the severity of the disease, the form of drug, and the route and period of administration, and may be 0.0001 to 50 mg/kg/day or 0.001 to 50 mg/kg/day. The pharmaceutical composition may be administered once or several times a day. The dose is not intended to limit the scope of the present disclosure in any way. The pharmaceutical composition according to the present disclosure may be formulated as pills, sugar-coated tablets, capsules, liquids, gels, syrups, slurries, or suspensions.

According to another embodiment of the present disclosure, there is provided a food composition for alleviating gallbladder disease containing, as an active ingredient, a compound represented by the following formula 1 or formula 2:

[Formula 1]

[Formula 2]

wherein $R_1$ is a $C_1$-$C_6$ alkyl group;

$R_2$ is selected from the group consisting of a $C_5$-$C_{10}$ aryl group, a $C_5$-$C_{10}$ heteroaryl group, and —C(=O)$R_5$;

$R_3$ is a $C_1$-$C_6$ alkyl group;

$R_4$ is selected from the group consisting of a $C_1$-$C_6$ alkyl group and a $C_3$-$C_6$ cycloalkyl group;

$R_5$ is a $C_5$-$C_8$ aryl group or a $C_5$-$C_8$ heteroaryl group; and the alkyl group of $R_1$ and $R_3$, the aryl group and heteroaryl group of $R_2$, the alkyl group and cycloalkyl group of $R_4$, and the aryl group and heteroaryl group of $R_5$ may be each independently unsubstituted or substituted with one or more $C_1$-$C_6$ alkyl groups and if substituted with a plurality of substituents, these substituents may be identical or different.

In the present disclosure, when $R_1$ is a methyl group, the compound is less toxic and shows a high gallstone dissolution rate. Thus, $R_1$ is preferably a methyl group, but is not limited thereto.

In the present disclosure, when $R_2$ is selected from the group consisting of a pyridinyl group, a pyrimidinyl group and a benzoyl group, the compound is less toxic and shows a high gallstone dissolution rate. Thus, $R_2$ is preferably selected from the group consisting of a pyridinyl group, a pyrimidinyl group and a benzoyl group, but is not limited thereto.

In the present disclosure, when $R_3$ is a methyl group, the compound is less toxic and shows a high gallstone dissolution rate. Thus, $R_3$ is preferably a methyl group, but is not limited thereto.

In the present disclosure, when $R_4$ is a cyclopropyl group, the compound is less toxic and shows a high gallstone dissolution rate. Thus, $R_4$ is preferably a cyclopropyl group, but is not limited thereto.

In the present disclosure, the compound represented by formula 1 is preferably 2-methoxy-6-methylpyridine represented by the following formula 3, or methyl 3-methylbenzoate represented by the following formula 4, but is not limited thereto:

[Formula 3]

[Formula 4]

In the present disclosure, the compound represented by formula 2 is preferably 1-cyclopropylethanone represented by the following formula 5, but is not limited thereto:

[Formula 5]

In the present disclosure, the compound can dissolved gallstones, thereby preventing or treating various gallbladder diseases that can be caused by gallstones.

Here, the gallstone may be cholesterol stone or pigmented stone.

In the present disclosure, the 2-methoxy-6-methylpyridine, methyl 3-methylbenzoate and 1-cyclopropylethanone compounds can effectively dissolve cholesterol stones and pigmented stones.

In addition, in the present disclosure, the compound represented by formula 1 or formula 2 is preferable because it does not form an epoxide even when it is stored for a long period of time. In addition, it has a boiling point of 80 to 160° C., and thus has an advantage in that it is not volatilized in the body or the rate of vaporization thereof is extremely low, indicating that it has less side effects.

In the present disclosure, the gallbladder disease whose symptoms can be alleviated by the compound represented by formula 1 or formula 2 may include one or more disease selected from the group consisting of asymptomatic cholelithiasis, biliary colic, cholecystitis, choledocholithiasis, and biliary pancreatitis, but is not limited thereto.

The food composition of the present disclosure may be prepared as various foods, for example, beverages, gums, teas, vitamin complexes, powders, granules, tablets, capsules, confectionery, cakes, bread and the like. The food composition of the present disclosure comprises a plant extract having little or no toxicity and side effects, and thus can be used with confidence even when it is administered for a long period of time for preventive purposes.

In the present disclosure, when the compound represented by formula 1 or 2 is contained in the food composition, it may be added in an amount of 0.1 to 50 wt % based on the total weight.

When the food composition is prepared as a beverage, there is no particular limitation, except that the beverage contains the food composition at the indicated percentage. The beverage may additionally contain various flavorings or natural carbohydrates, like conventional beverages. Specifically, the natural carbohydrates include monosaccharides such as glucose, disaccharides such as fructose, polysaccharides such as sucrose, conventional sugars such as dextrin, cyclodextrin or the like, and sugar alcohols such as xylitol, sorbitol, erythritol or the like. Examples of the flavorings include natural flavorings (thaumatin, *stevia* extracts, such as rebaudioside A, glycyrrhizin, etc.) and synthetic flavorings (saccharin, aspartame, etc.).

In addition, the food composition of the present disclosure may contain various nutrients, vitamins, minerals (electrolytes), flavorings such as synthetic flavorings and natural flavorings, colorants, pectic acid and its salt, alginic acid and its salt, organic acids, protective colloidal thickeners, pH adjusting agents, stabilizers, preservatives, glycerin, alcohol, carbonizing agents that are used in carbonated beverages, etc.

Such components may be used individually or in combination. Although the content of such additives is not of great importance, it is generally selected in a range of 0.1 to about 50 parts by weight based on 100 parts by weight of the food composition of the present disclosure.

Hereinafter, the present disclosure will be described in detail with reference to examples. However, these examples are only illustrative of the present disclosure, and the scope of the present disclosure is not limited by these examples.

EXAMPLES

[Preparation Example] Preparation of Gallstone-Dissolving Agents 1 g of each of the compounds shown in Table 1 below was dissolved in 1 ml of each of dimethyl sulfoxide, thereby preparing gallstone-dissolving agents.

TABLE 1

| Classification | Example 1 | Example 2 | Example 3 | Comparative Example 1 | Comparative Example 2 |
|---|---|---|---|---|---|
| Component | 2-methoxy-6-methylpyridine | methyl 3-methylbenzoate | 1-cyclopropylethanone | Methyl tert-butyl ether | ethyl propionate (EP) |

[Experimental Example 1] Evaluation of Gallstone Dissolution

In order to evaluate the cholesterol stone and pigmented stone dissolution abilities of each of Examples 1 to 3 and Comparative Examples 1 and 2 prepared according to the Preparation Example above, cholesterol stones and pigmented stones removed during surgery of gallstone patients were obtained, thereby preparing gallstones. 0.5 g of each of the prepared gallstones was placed in an Eppendorf tube, and then 0.5 ml of each of the gallstone-dissolving agents of Examples 1 to 3 and Comparative Examples 1 and 2 was added to the Eppendorf tube containing the gallstone. Each tube was left to stand at 37° C. for 4 hours. Thereafter, the gallstone dissolution ability of each compound was evaluated by measuring the mass of the gallstones before and after dissolving the gallstone by treatment with each compound. The results of evaluating the abilities to dissolve cholesterol stones and pigmented stones are shown in Tables 2 and 3 below, respectively, and photographs before and after dissolving the gallstones are comparatively shown in FIGS. 1 and 2, respectively.

The gallstone dissolution ability was calculated using the following equation:

Gallstone dissolution ability (%)=(weight of gallstone after dissolution)/(weight of gallstone before dissolution)×100

TABLE 2

| Classification | Dissolution ability (%) Cholesterol stone |
|---|---|
| Example 1 | 14.16% |
| Example 2 | 10.00% |
| Example 3 | 28.57% |
| Comparative Example 1 | 24.07% |
| Comparative Example 2 | 48.66% |

TABLE 3

| Classification | Dissolution ability (%) Pigmented stone |
|---|---|
| Example 1 | 52.92% |
| Example 2 | 58.33% |
| Example 3 | 60.00% |

Figure 1:
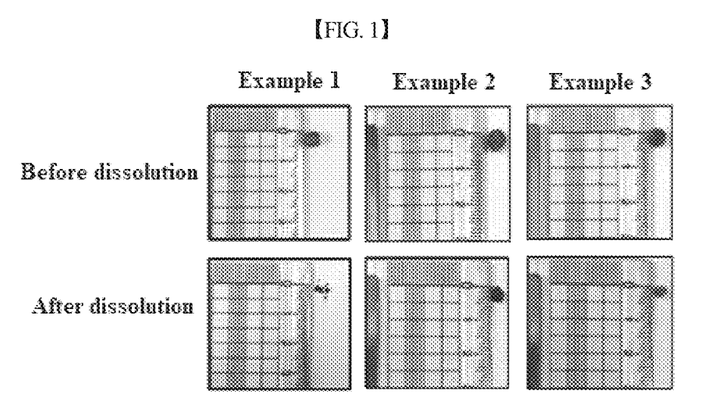
FIG. 1 shows photographs before and after dissolving cholesterol stone using gallstone-dissolving agents of Examples 1 to 3.

As a result, as shown in Table 2 above and FIG. 1, it can be confirmed that when the compounds of Examples 1 to 3 were used, they had an excellent ability to dissolve the cholesterol stone, compared to Comparative Example 1 or 2. Particularly, it can be seen that Example 2 had an excellent ability to dissolve the cholesterol stone.

Figure 2:
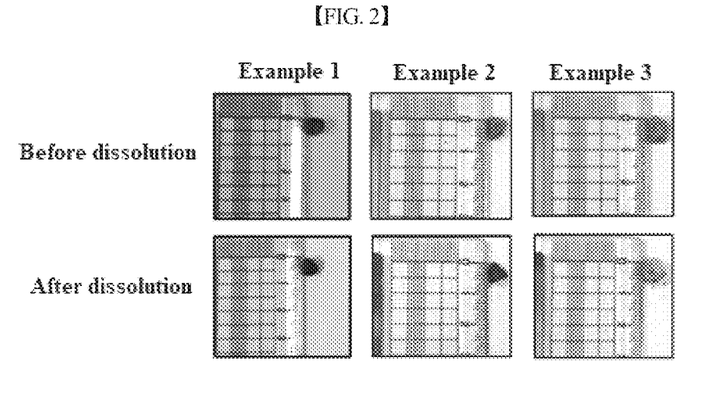
FIG. 2 shows photographs before and after dissolving pigmented stone using gallstone-dissolving agents of Examples 1 to 3.

In addition, as shown in Table 3 above and FIG. 2, it can be confirmed that when the compounds of Examples 1 to 3 were used, they had an excellent ability to dissolve the pigmented stone.

[Experimental Example 2] Evaluation of Gallbladder Epithelial Cell Cytotoxicity

Using gallbladder epithelial cells from the gallbladders of patients who underwent cholecystectomy, evaluation of the gallbladder epithelial cell cytotoxicity of Examples 1 to 3 and Comparative Example 1 was performed. First, $1\times10^4$ gallbladder epithelial cells were dispensed into each well of a 96-well dish, and treated with various concentrations (5% and 10%) of each of the Examples and the Comparative Example, and then incubated for 24 hours. A control for the cytotoxicity evaluation was incubated in a medium containing dimethyl sulfoxide as a vehicle.

Next, each well treated with each of Examples 1 to 3, Comparative Example 1 and the control was 10 μl of EZ-Cytox. After reaction in an incubator for 2 hours, the plate was shaken for 1 minute before measurement of absorbance, and the absorbance at 450 nm was measured using a 96-well plate reader.

Figure 3:
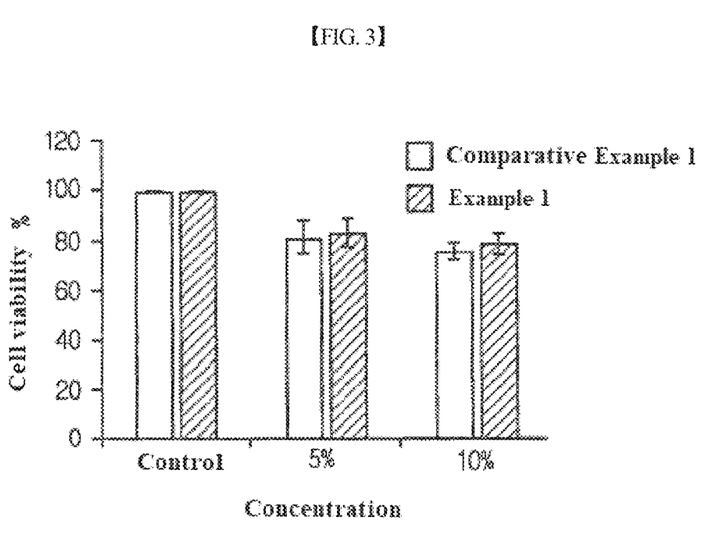
FIG. 3 is a graph showing the results of evaluating the gallbladder epithelial cell cytotoxicity of Example 1 at various concentrations.
Figure 4:
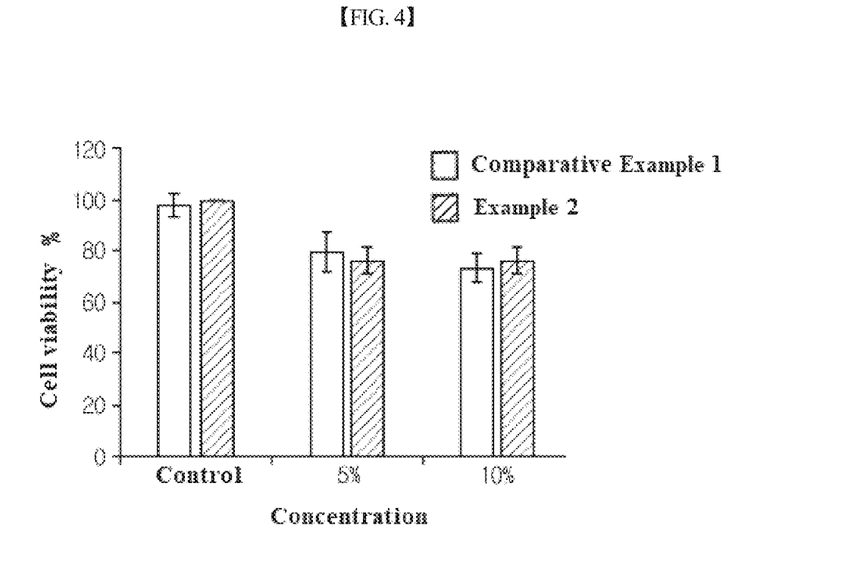
FIG. 4 is a graph showing the results of evaluating the gallbladder epithelial cell cytotoxicity of Example 2 at various concentrations.
Figure 5:
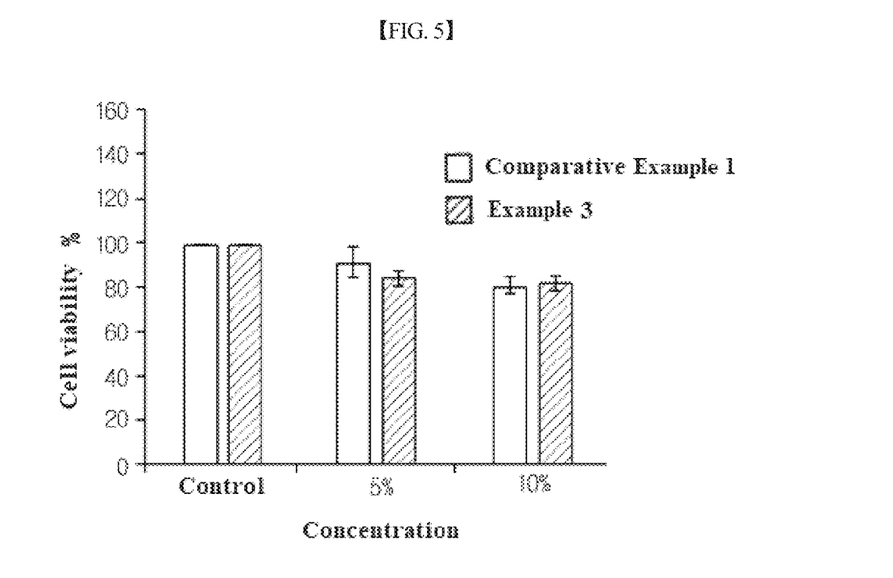
FIG. 5 is a graph showing the results of evaluating the gallbladder epithelial cell cytotoxicity of Example 3 at various concentrations.

As a result, as shown in FIGS. 3 to 5, it can be confirmed that Examples 1 to 3 had no cytotoxicity at a level equal to or higher than that of Comparative Example 1.

Although the preferred embodiments of the present disclosure have been described in detail above, it will be obvious to those skilled in the art that the scope of the present disclosure is not limited to these embodiments and that various modifications and changes are possible without departing from the technical spirit of the present disclosure as defined in the appended claims.

INDUSTRIAL APPLICABILITY

The present disclosure relates to a pharmaceutical composition for treating gallbladder disease containing a gallstone-dissolving agent, and more particularly to a pharmaceutical composition for treating gallbladder disease containing a gallstone-dissolving agent having the effect of dissolving gallstone, a cause of the gallbladder disease.

The invention claimed is:

1. A method for treating gallbladder disease comprising administering to a subject an effective amount of a compound represented by the following formula 1:

[Formula 1]

wherein
$R_1$ is a $C_1$-$C_6$ alkyl group;
$R_2$ is a pyridinyl group; and
the alkyl group of $R_1$ and the pyridinyl group of $R_2$ may be each independently unsubstituted or substituted with one or more $C_1$-$C_6$ alkyl groups.

2. The method of claim 1, wherein $R_1$ is a methyl group.

3. The method of claim 1, wherein the compound represented by formula 1 is 2-methoxy-6-methylpyridine.

4. The method of claim 1, wherein the compound has a boiling point of 80 to 160° C.

5. The method of claim 1, wherein the compound dissolves gallstone comprising cholesterol stone or pigmented stone.

6. The method of claim 1, wherein the gallbladder disease includes one or more diseases selected from the group consisting of asymptomatic cholelithiasis, biliary colic, cholecystitis, choledocholithiasis, and biliary pancreatitis.

* * * * *